United States Patent [19]

Liebermann

[11] 4,138,879
[45] Feb. 13, 1979

[54] SIGHTLESS BUBBLE DETECTOR

[75] Inventor: Leonard N. Liebermann, La Jolla, Calif.

[73] Assignee: Tif Instruments, Inc., Miami, Fla.

[21] Appl. No.: 826,689

[22] Filed: Aug. 22, 1977

[51] Int. Cl.² ........................................... G01N 29/02
[52] U.S. Cl. ........................................ 73/19; 73/61 R
[58] Field of Search ........................... 73/19, 53, 61 R; 62/125, 126, 127

[56] References Cited

U.S. PATENT DOCUMENTS

| 2,573,390 | 10/1951 | Blanchard | 73/19 X |
| 3,974,681 | 8/1976 | Namery | 73/19 |
| 4,015,464 | 4/1977 | Miller et al. | 73/61 |

*Primary Examiner*—Herbert Goldstein
*Attorney, Agent, or Firm*—Pennie & Edmonds

[57] ABSTRACT

A detector comprises a pair of electromechanical transducers for disposition on a fluid-filled conduit in an acoustically coupled relationship, an adjustable gain driving amplifier responsive to the electrical output of one transducer for driving the other transducer, an automatic gain control circuit for automatically adjusting the gain of the driving amplifier maintaining the system on the margin of oscillation, and an indicating circuit for detecting modulation of the driving signal. Bubbles passing through the conduit increase the gain required to maintain the system on the margin of oscillation, and are detected as modulations of the driving signal. In a preferred embodiment, this bubble detector is utilized as a refrigerating system test instrument.

15 Claims, 4 Drawing Figures

SIGHTLESS BUBBLE DETECTOR

BACKGROUND OF THE INVENTION

This invention relates to a device for detecting inhomogeneities such as gas bubbles in a fluid in a conduit such as a liquid and, more particularly, to a device for detecting bubbles in liquid-filled pipes.

The detection of inhomogeneities such as bubbles within a fluid for example a liquid is of importance in monitoring and controlling a wide variety of processes. In high temperature processes using liquid coolants, for example, the presence of inhomogeneities in the form of bubbles can indicate regions of heat transfer deterioration. As another example, in refrigeration systems the presence of bubbles provides an indication of refrigerant insufficiency.

The usual technique for detecting bubbles within a pipe or conduit, however, is visual observation through a sight glass or other window. This technique requires a human observer and is not readily automated. Moreover, it cannot be used in much existing equipment, such as many automotive and home air conditioners which have no sight glasses or viewing windows.

In the instance of automotive and home air conditioners, the unavailability of sightless bubble detectors has contributed to a definite environmental problem. Upon suspicion of refrigerant insufficiency, it is common practice to empty all of the refrigerant gas, usually freon, into the atmosphere and to refill the system with the factory specified amount. The discharge of such gases into the atmosphere has a now well-recognized detrimental effect on the earth's protective ozone layer. See the Report of the Federal Task Force on Inadvertent Modification of the Stratosphere, *Fluorocarbons and the Environment* (U.S. Gov't., 1975).

While devices exist for automatically monitoring the bubble content of relatively large samples of open water, these devices are inappropriate for the non-obstructive monitoring of liquids contained in small diameter pipe or conduit. U.S. Pat. No. 3,046,780, for example, issued to the present inventor on July 31, 1962, discloses a fluid condition monitor comprising a towable acoustic resonator and a pair of coupled transducers. Impurities or disturbances in the fluid through which the device is towed are detected by variations in the quality factor, Q, of the resonating system. While it is suggested that this device can be used in pipelines, it would clearly be preferable to utilize a detection device which need not be placed within the pipe or conduit and thereby obstruct or impede fluid flow. Moreover, many pipes and conduits of interest have a sufficiently small diameter that impractically small resonators and impractically high frequency transducers would be required.

SUMMARY OF THE INVENTION

In accordance with the present invention, a detector comprises a pair of electromechanical transducers for disposition on a fluid-filled conduit in an acoustically coupled relationship, an adjustable gain driving amplifier responsive to the electrical output of one transducer for driving the other transducer, an automatic gain control circuit for automatically adjusting the gain of the driving amplifier maintaining the system on the margin of oscillation, and an indicating circuit for detecting modulation of the driving signal. Inhomogeneities such as bubbles passing through the conduit near the transducers cause variations, for example an increase, in the gain required to maintain the system on the margin of oscillation, and are detected as modulations of the driving signal. In a preferred embodiment, this detector is utilized as a refrigeration test instrument. The advantages of this detector are (1) it does not require a sight glass or window for visual observation; (2) it does not obstruct the flow of fluid; (3) it does not require penetration of the conduit; and (4) it can be readily incorporated into automatic monitoring systems.

BRIEF DESCRIPTION OF THE DRAWINGS

The nature, advantages, and various features of the invention will appear more fully upon consideration of the illustrative embodiments now to be described in detail in connection with the accompanying drawings.

In the drawings.

For convenience of reference, similar elements are denoted by the same reference numeral throughout the drawings.

DETAILED DESCRIPTION OF THE DRAWINGS

Figure 1:
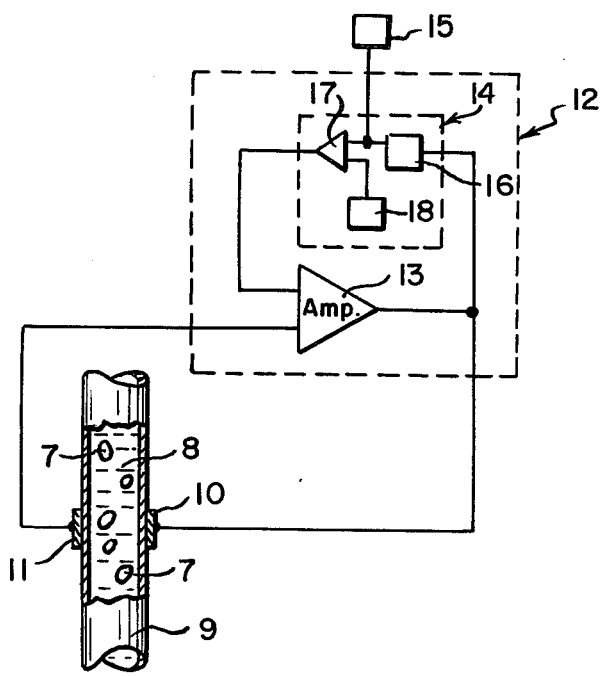
FIG. 1 is a schematic block diagram of a bubble detection device in accordance with the invention.

Referring to the drawings, FIG. 1 schematically illustrates a detector in accordance with the invention for detecting gas bubbles or other inhomogeneities in a liquid or other fluid 8 within pipe or conduit 9. In substance, the detector comprises a pair of electromechanical transducers 10 and 11, a feedback driving circuit with automatic gain control 12 comprising driving amplifier 13, such as an operational amplifier, and automatic gain control circuit 14, and an indicating circuit 15.

Transducers 10 and 11 are preferably barium titanate crystals cut and mounted to respectively transmit and receive compressional vibrations. Preferably, they are coupled to the pipe by rubber mountings (not shown) for rejecting shear oscillations.

Automatic gain control circuit 14 (AGC circuit) is a circuit arrangement well-known in the art for preventing swings in the output of an amplifier, such as driving amplifier 13, beyond a predefined excursion range. It consists essentially of a feedback conditioning circuit 16, such as a half-wave detector, for defining the feature of the output of driving amplifier 13 to be constrained, a feedback amplifier 17, and a sensitivity control 18.

In the preferred operation of the device of FIG. 1, acoustic waves from transmitting transducer 10 pass through conduit 9, liquid 8, and any bubbles passing between or near to the two transducers to receiving transducer 11. Receiving transducer 11 converts the received acoustic waves into electrical signals which inturn are applied to the input of AGC controlled driving amplifier 13.

The AGC circuit 14, responsive to the output of amplifier 13, is adjusted to maintain the system comprising the transducers and the driving amplifier at a predetermined operating point. Preferably, for maximum sensitivity, the AGC circuit is adjusted to maintain the system on the margin of oscillation. Should inhomogeneities such as bubbles pass between or near transducers 10 and 11, the acoustic signal reaching transducer 11 will be altered by the different acoustic properties of the inhomogeneity, for example, the signal will be attenuated by the higher acoustic absorption of a gas in a liquid resulting in an attenuated electrical input to amplifier 13. AGC circuit 14 alters the gain of amplifier 13, as necessary, to produce a change in the driving signal that will quickly restore the system to its operating point on the margin of oscillation. The resulting changes in the driving signal can be conveniently metered by indicator 15 monitoring the output of amplifier 13.

Figure 2:
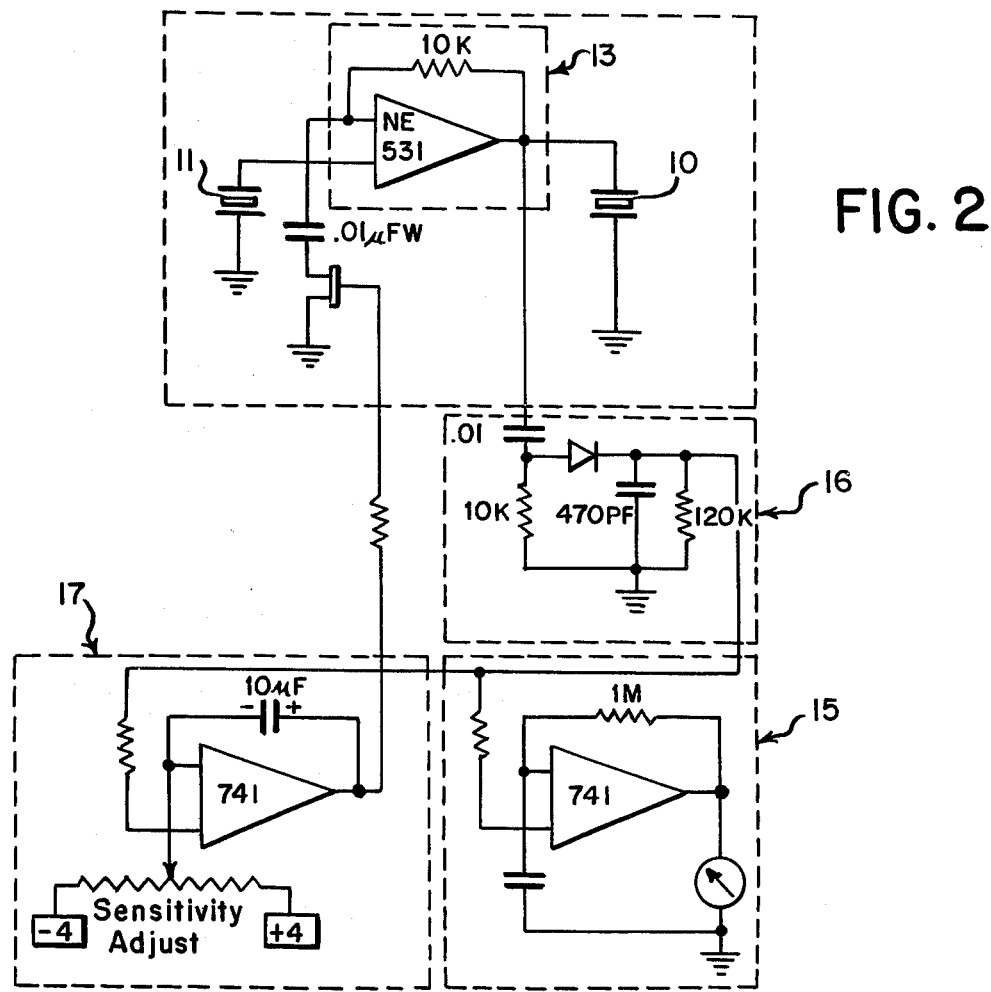
FIG. 2 is a circuit diagram of a preferred feedback driving circuit for the device of FIG. 1.

FIG. 2 shows a detailed circuit diagram of a preferred feedback driving circuit for this device. Here the output of driving amplifier 13 is applied to half-wave detector 16 for conditioning in accordance with its average half-wave value. Indicator circuit 15 is a conventional circuit for receiving this average half-wave value from the output of circuit 16, amplifying it for display and displaying it on a voltmeter. Feedback amplifier 17 is a simple differential amplifier with a potentiometer sensitivity adjustment. The components in this circuit are all standard items and have the manufacturer's type numbers and values of resistance and capacitance set forth in the drawing. This circuit is designed to operate at a frequency of about 200 kilohertz.

As can be readily appreciated, this detector does not require a sight glass or a window for visual observation of the liquid or other fluid within the conduit. It does not obstruct the flow of fluid in the conduit, nor does it require penetration of the conduit. Furthermore, since inhomogeneities are detected as variations in an electrical signal, the detector can be readily incorporated into automatic monitoring systems.

Figure 3:
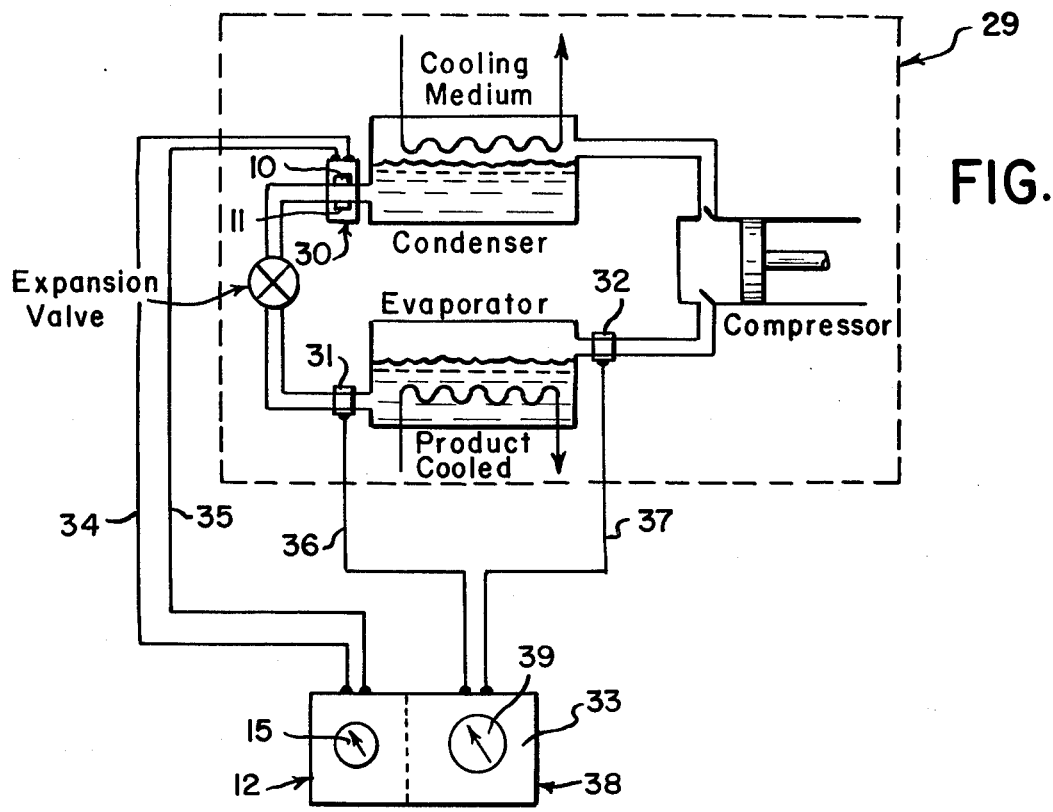
FIG. 3 is a circuit diagram of a preferred automatic refrigeration test instrument employing the bubble detection device of FIGS. 1 and 2.

FIG. 3 schematically illustrates a refrigeration test instrument, in accordance with a further embodiment of the invention, for diagnosing the state of a refrigerating system 29. Specifically, the test instrument comprises a bubble detector of the type shown in FIGS. 1 and 2 with transducers 10 and 11 preferably mounted in clamp 30 for disposition on the refrigerant tube and a pair of contact temperature sensors 31 and 32 for disposition in contact with the refrigerant tube on either side of the evaporator. Conveniently, the transducers and the temperature sensors are electrically connected to a circuit box 33 by flexible wires 34, 35, 36 and 37, respectively.

In a preferred embodiment, temperature sensors 31 and 32 are silicon diodes whose voltage drop, as is well-known, is a linear function of temperature. A temperature differential indicating circuit 38 is conveniently provided in box 33 for determining the difference between the sensed temperature and displaying on a meter 39.

Figure 4:
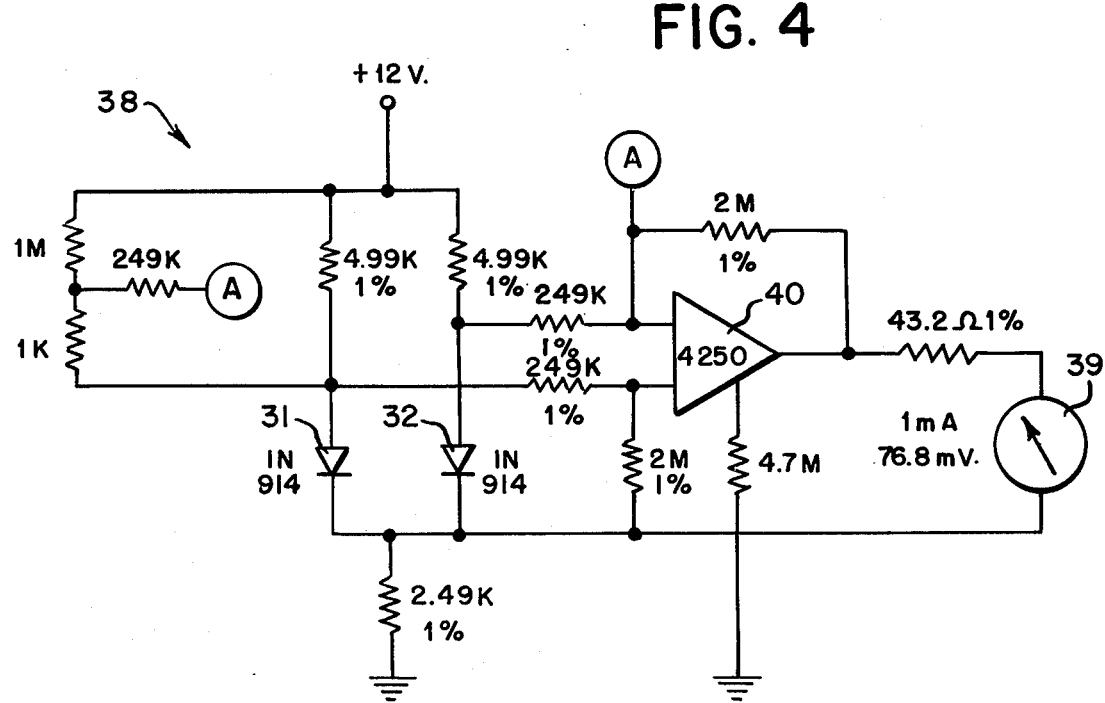
FIG. 4 is a circuit diagram of a preferred temperature sensing circuit useful in the embodiment of FIG. 3.

FIG. 4 illustrates a preferred temperature differential indicating circuit 38. Diodes 31 and 32 are disposed in thermal contact with the refrigerant tube at the input and output of the evaporator, respectively. A voltage is applied across the diodes, and circuit means in the form of differential amplifier 40 and meter 39 is provided for detecting, amplifying, and displaying the temperature-induced difference in voltage drops across the diodes 31 and 32. The components of this circuit are all standard items and have the manufacturer's type numbers and values of resistance and capacitance set forth in the drawing.

In operation, the temperature sensors are disposed on the refrigerant input conduit to the evaporator and the output conduit. If the evaporator is filled with refrigerant, the temperature difference between the input and the output will be zero or negative, i.e., the output being lower in temperature than the input. If the temperature difference is positive, the amount of refrigerant may be inadequate but is not necessarily so. This ambiguity is resolved by applying the bubble detector to the refrigerant conduit in one of three places: near the condenser output, near the expansion valve, or, in capillary systems, near the capillary tube. If bubbles are detected, the system requires additional refrigerant. If no bubbles are detected, they must be made to occur, as by inhibiting cooling air to the condenser, and the temperature difference should be tested again under these new conditions. The refrigerant change is adequate under these conditions only if the temperature differential is zero or negative.

While the invention has been described in connection with only a small number of specific embodiments, it is to be understood that these are merely illustrative of the many other specific embodiments which can also utilize the principles of the invention. Numerous and varied devices can be made by those skilled in the art without departing from the spirit and scope of the present invention, as defined by the following claims.

I claim:

1. A device for detecting inhomogeneities in a fluid within a conduit comprising: a pair of electromechanical transducers for disposition on such conduit in an acoustically coupled relationship; adjustable gain driving amplifier means responsive to the electrical output of one of said transducers for providing a driving signal for driving the other of said transducers; automatic gain control circuit means connected to the output and at least one input of said driving amplifier means for automatically adjusting the gain of said driving amplifier to maintain said transducers and said amplifiers at a predetermined operating point; and indicating circuit means connected to said amplifier for indicating changes in said driving signal caused by an inhomogeneity in said fluid moving past said transducers.

2. A device according to claim 1 wherein said automatic gain control circuit comprises means for automatically adjusting the gain of said driving amplifier for maintaining the system comprising said transducers and said amplifier on the margin of oscillation.

3. A device according to claim 1 wherein said transducers comprise transducers adapted for selectively transmitting compressional vibrations and rejecting shear oscillations.

4. A device according to claim 1 wherein said driving amplifier is an operational amplifier.

5. A device according to claim 1 wherein said automatic gain control circuit means comprises a feedback conditioning circuit, a feedback amplifier, and a sensitivity control.

6. A device according to claim 5 wherein said feedback conditioning circuit comprises a half-wave detector.

7. A device for testing refrigerating systems of the type utilizing a refrigerant, a refrigerant tube and an evaporator, said device comprising: temperature differential sensing means for detecting a difference in the temperature of such refrigerant between the input and the output of such evaporator; indicating circuit means connected to said sensing means for indicating the detected temperature difference; and a detecting device for detecting inhomogeneities in such refrigerant within such refrigerant tube, said device comprising (1) a pair of electromechanical transducers for disposition on such refrigerant tube in an acoustically coupled relationship; (2) adjustable gain driving amplifier means responsive to the electrical output of one of said transducers for providing a driving signal for driving the other of said transducers; automatic gain control circuit means connected to the output and at least one input of said driving amplifier means for automatically adjusting the gain of said driving amplifier to maintain the system comprising said transducers and said amplifier at a predetermined operating point; and indicating circuit means connected to said amplifier for indicating changes in said driving signal caused by an inhomogeneity in such refrigerant moving part said transducers whereby the operating condition of said refrigerating system may be determined.

8. A device according to claim 7 wherein said automatic gain control circuit comprises means for automatically adjusting the gain of said driving amplifier for maintaining the system comprising said transducers and said amplifier on the margin of oscillation.

9. A device according to claim 7 wherein said temperature differential sensing means comprises (1) a pair of diodes for disposition in thermal contact with such refrigerant tube at the input and output of such evaporator, respectively; (2) means for applying voltage across said diodes; and (3) means for detecting the difference in voltage drops across said diodes.

10. A device for detecting inhomogeneities in a fluid within a conduit comprising: a pair of electromechanical transducers for disposition on such conduit in a acoustically coupled relationship; driving amplifier means responsive to the electrical output of one of said transducers for providing a driving signal for driving the other of said transducers; means for automatically adjusting the system comprising said amplifier and said transducers to a predetermined operating point in response to a change in said operating point caused by an inhomogeneity in such fluid moving past said transducers; and means for detecting changes in said operating point.

11. A device according to claim 10 wherein: said driving amplifier means is an adjustable gain driving amplifier; and said means automatically adjusting said system comprises means for adjusting the gain of said driving amplifier.

12. A device according to claim 10 wherein said means for automatically adjusting said system to a predetermined operating point comprises means for adjusting said system to an operating point on the margin of oscillation.

13. A device for testing refrigerating systems of the type utilizing a refrigerant, a refrigerant tube and an evaporator said device comprising: temperature differential sensing means for detecting the temperature of such refrigerant at the input and the output of such evaporator; indicating circuit means connected to said sensing means for indicating the difference between said temperatures and a bubble detecting device for detecting bubbles in refrigerant within such refrigerant tube, said device comprising (1) a pair of electromechanical transducers for disposition on such refrigerant tube in an acoustically coupled relationship; (2) driving amplifier means responsive to the electrical output of one of said transducers for providing a driving signal for driving the other of said transducers; means for automatically adjusting the system comprising said amplifier and said transducers to a predetermined operating point in response to a change in said operating point caused by a bubble in said refrigerant moving past said transducers; and means for detecting changes in said operating point, whereby the indicated temperature difference and detection of bubbles establish the operating condition of such refrigeration system.

14. A device according to claim 13 wherein said driving amplifier means is an adjustable gain driving amplifier and said means for automatically adjusting said system comprises means for adjusting the gain of said driving amplifier.

15. A device according to claim 13 wherein said means for automatically adjusting said system to a predetermined operating point comprises means for adjusting said system to an operating point on the margin of oscillation.

* * * * *